United States Patent [19]

Steer

[11] Patent Number: 4,645,500
[45] Date of Patent: Feb. 24, 1987

[54] NON-RETURN VALVE ASSEMBLY

[75] Inventor: Peter L. Steer, Surrey, England

[73] Assignee: Craig Medical Products Limited, Reigate, England

[21] Appl. No.: 794,880

[22] Filed: Nov. 4, 1985

[30] Foreign Application Priority Data

Nov. 23, 1984 [GB] United Kingdom ............... 8429645

[51] Int. Cl.⁴ .......................................... A61F 13/16
[52] U.S. Cl. ............................... 604/378; 137/512.15; 604/369
[58] Field of Search ..................... 604/358, 383, 378; 405/19; 210/136; 137/512.15

[56] References Cited

U.S. PATENT DOCUMENTS

| | | |
|---|---|---|
| 3,556,102 | 1/1971 | Davis . |
| 3,814,101 | 6/1974 | Kozak . |
| 3,930,096 | 12/1975 | Gilpatrick ..................... 137/512.15 |
| 4,002,034 | 1/1977 | Muhring et al. ............... 137/512.15 |
| 4,055,180 | 10/1977 | Karami . |
| 4,246,901 | 1/1981 | Frosch . |

FOREIGN PATENT DOCUMENTS

| | | |
|---|---|---|
| 0093175 | 11/1983 | European Pat. Off. . |
| 0117351 | 9/1984 | European Pat. Off. . |
| 0122803 | 10/1984 | European Pat. Off. . |
| 3301555 | 8/1984 | Fed. Rep. of Germany ...... 604/358 |
| 910837 | 11/1962 | United Kingdom . |
| 1011517 | 12/1965 | United Kingdom . |
| 1059680 | 2/1967 | United Kingdom . |
| 1144483 | 4/1969 | United Kingdom . |
| 1289102 | 9/1972 | United Kingdom . |
| 2072512 | 10/1981 | United Kingdom . |
| 2135892 | 3/1983 | United Kingdom . |
| 2135893 | 3/1983 | United Kingdom . |
| 2138303 | 1/1984 | United Kingdom . |
| 2126099 | 3/1984 | United Kingdom . |
| 2126902 | 4/1984 | United Kingdom . |

Primary Examiner—Lowell A. Larson
Attorney, Agent, or Firm—Lawrence S. Levinson; Sanford J. Asman

[57] ABSTRACT

A non-return valve assembly particularly for an incontinence device, includes a least three layers, the layers being secured together, the first layer being a sheet or film of perforated material, and the second layer is a sheet or film of material having cuts therein defining an array of flap valves. The third layer is a material having holes therein, each hole being in registry with an associated flap valve and being of a size to accommodate the flap of said valve. The flap valves may be arranged in a regular rectangular array and each flap of a valve is defined by three cuts in the sheet material, the cuts constituting three sides of a rectangle so that the flap of the valve can pivot out of the plane of the sheet material generally about a notional axis formed by the fourth side of the rectangle.

14 Claims, 7 Drawing Figures

NON-RETURN VALVE ASSEMBLY

BACKGROUND OF THE INVENTION

This invention relates to a non-return valve assembly. This is particularly but not exclusively useful for incorporation in an incontinence appliance.

Over the years, there have been numerous attempts to provide incontinence appliances and incontinence devices for use in receiving or conducting away urine from persons afficted with incontinence. In British Pat. No. 910837 published in 1962 there was a proposal whereby a pad could be pumped up by air pressure so that it pressed on a location adjacent the patient's perinium and ischiorectal area in order to close off the patient's bladder outlet. In British Pat. Nos. 1,011,517 and 1,059,680 the use of suction to remove discharged urine through a rubber suction head was proposed. British Pat. No. 1,144,483 published in 1969 and U.S. Pat. No. 3,556,102 published in 1971 are examples of arrangements having a pad or rim surrounding a central hole which leads to a bag for containing discharged urine. There are many other proposals based on this principle. British Pat. No. 1,289,102 published in 1972 discloses the employment of a urine collecting bag having a one-way valve disposed at or adjacent the inlet to the bag; the one-way valve is constituted by a flat tube of moisture impermeable plastics material. The valve has a top opening and a bottom outlet and the latter has a pocketed flap intended to prevent return flow of urine. More recently, proposals have been made for the use of various kinds of pad for wear over the urinary organ.

In British Patent application Ser. No. 2,072,512 the present inventor disclosed a female incontinence device comprising a pad of closed cell resilient impact absorbing polyurethane elastomer which has a central hole. A funnel is in communication with the hole and discharged urine is conducted away by a tube. U.K. Patent application Ser. No. 2,126,099 published March 1984 discloses a female urine collection device having a cup-shaped chamber with a flexible lip on its periphery. A duct leads to a section of flexible tubing. The tubing leads to a collection reservoir and acts as a non-return valve. The receiving chamber and reservoir are mounted in a housing of soft absorbent material. This material is apparently intended to provide external cushioning and the device is disclosed as suitable for receiving involuntary urine discharges. It would not appear to be capable of accommodating substantial volume flows.

U.K. Patent applications Ser. No. 2,135,892 and 3 disclose designs of absorbent pads which may be used as sanitary napkins. U.K. Patent application Ser. No. 2,138,303 and European application Ser. No. 122803 both disclose an incontinence device consisting of a pad of absorbent material incorporating along its upper surface a strip of a skeleton polyester foam material. The function of this is to enable urine to flow rapidly to the surface of those regions of the pad not immediately saturated. In U.S. Pat. No. 4,246,901 the use of a wicking material to absorb urine is disclosed, and a similar concept is present in European Patent application Ser. No. 117351. This suggests that an incontinence pad comprises an absorbent layer with a porous water retardant embossed fibrous sheet overlying the absorbent layer. The product is worn with the embossed sheet adjacent to the wearer and this sheet is intended to reduce fluid strike through to the outer surface of the absorbtive product while allowing the product to breathe.

In European application Ser. No. 93175 the inventor suggests that the use of a resin to absorb urine within a bag by a gelling action.

It will be appreciated that the wearer of an incontinence device can be greatly inconvenienced, and there can be undesired medical problems if the surface of the device can remain damp or have any significant quantity of moisture and this problem is exacerbated by the difficulty of preventing back-flow of discharged urine. In other words, while the prior art is replete with attempts to prevent discharged urine from again contacting the skin of the patient, these attempts have normally been unsuccessful in practice.

SUMMARY OF THE INVENTION

According to the invention, there is provided a non-return valve assembly which includes at least three layers, the layers being secured together, the first layer being a sheet of film of perforated material, the second layer being a sheet or film of material having cuts therein defining an array of flap valves, and the third layer being a material having holes therein, each hole being in registry with an associated flap valve and being of a size to accommodate the flap of said valve.

In a preferred embodiment of the invention the flap valves are arranged in a regular rectangular array and each flap of a valve is defined by three cuts in the sheet material, the cuts constituting three sides of a rectangle so that the flap of the valve can pivot out of the plane of the sheet material generally about a notional axis formed by the fourth side of the rectangle. An equivalent effect can be obtained by other configurations of cuts in the sheet forming the second layer. For example the cuts could be V-shaped or made up by half or a major portion of the periphery of a circle or an ellipse.

The first layer may (but need not) be made of polyethylene or e.v.a. polyethylene copolymer, and it may have a thickness of about 0.006 to 0.010 inch (0.15 to 0.25 mm). The flap valves are preferably arranged in linear rows so that the three layers can be integrated together by linear plastics welds (or other linear securing means). The product so produced can be regarded as a one-piece generally flat non-return valve unit for use, particularly in incontinence applications, as a unit which can be secured to an absorbent pad of any suitable kind, there having been to the best of the Applicant's knowledge and belief no such unit hitherto available. It enables the designer of incontinence devices (or, indeed, other liquid receiving devices) to largely overcome the problem of high volume channelling of urine (liquid) over a restricted cross-sectional area, and instead achieve a more widespread distribution over a greater area of the absorbent material. Alternatively such a unit can be used with a conventional bag by placing a funnel structure of conducting away urine adjacent to its third layer.

In one particular embodiment of the invention, the third layer is placed adjacent to the surface of a pad of sponge material, e.g. compressed sponge material such as is available from Spontex Limited. Suitable urine-conducting structure may be arranged to convey urine from the third layer or from the base of a sponge layer to a conventional leg-bag. The valve assembly may be fixed to the pad but such fixing is not essential.

The invention will be better understood from the following non-limiting description of an example thereof given with reference to the accompanying drawings in which:

DETAILED DESCRIPTION OF THE DRAWINGS

The incontinence pad assembly illustrated in FIG. 1–5 includes a first layer A, a second layer B and a third layer C. While these layers are illustrated as rectangular, they may of course be of other shapes. The three layers are preferably all of synthetic plastics material, and preferably are integrated together by an array of bar welds or an array of spot welds. The first layer A is normally the top layer and provides the surface which is presented to the skin of the wearer. It is a perforated sheet material, perforated in such a way as to permit liquid to pass therethrough; preferably the perforations are of fairly small size, e.g. 0.5 mm or less in diameter.

Figure 1:
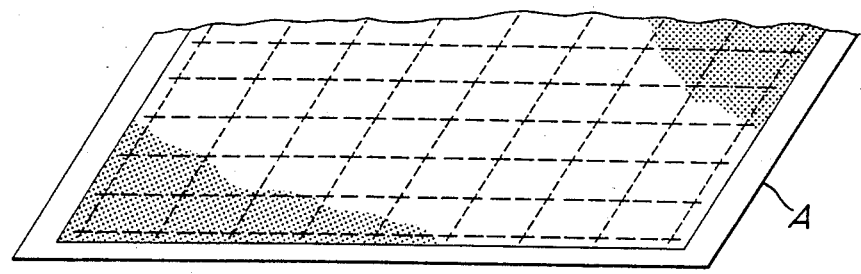
FIGS. 1–3 are perspective views respectively of first, second, and third layers used in an incontinence pad assembly according to one example of the invention.
Figure 2:
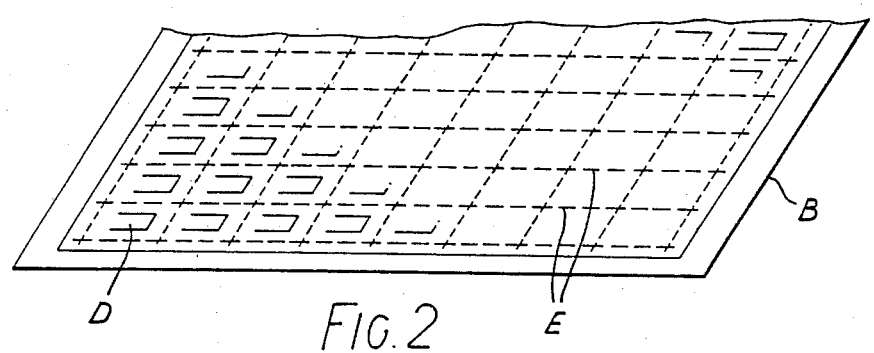
Figure 3:
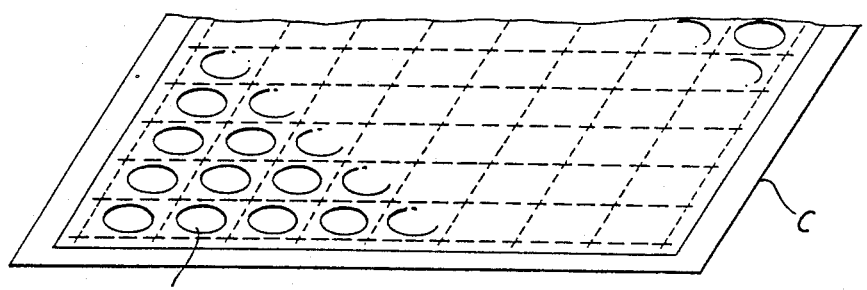
Figure 4:
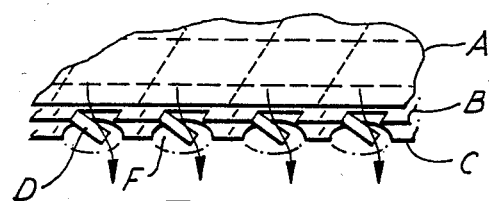
FIGS. 4 and 5 are diagrammatic edge views of one example of assembly according to the invention, illustrating respectively the urine flow condition when the flap valves are open and "no reverse flow" condition when the flap valves are closed.

The second layer B is the flap valve layer and consists of a sheet of synthetic plastics material having an array of flaps punched out in the manner illustrated. In other words, the sheet or film is operated upon either by punching or cutting to provide a plurality of flap valves preferably arranged in a rectangular array as illustrated. Each flap valve can be regarded as defined by a cut consisting of three sides of a rectangle, whereupon the fourth side of the rectangle acts as a connection of the flap to the remainder of the sheet. The flaps can be pivoted as seen in FIG. 4 to provide a flow path. In FIG. 4 a flap is seen at D. As seen in FIG. 2 the flaps are arranged in a linear array so as to allow securing means such as spot welds or interrupted bar welds to extend along in parallel lines, two of which are indicated at E. The layer B is preferably of a thickness of 0.006 to 0.010 inches, 0.15 to 0.25 mm. The layer A is preferably of a thickness 0.003 to 0.006 inches, 0.075 to 0.15 mm.

The layer C is a sheet of plastics material, of overall size substantially equal to that of layers A and B, having an array of holes therein, the holes passing completely through the thickness of the layer. One hole is denoted by F. The holes are arranged in registry with the flaps of the flap valves of FIG. 2. Each hole is of a size sufficient to readily accommodate a flap of a flap valve when pushed down thereinto, so as to permit liquid flow, but the relative sizes and configurations are chosen so that the flaps of the flap valves are not jammed or stuck down in the holes of the layer C. One flap of a flap valve is denoted by D. A preferred material for the layer C is soft ethylene vinyl acetate, and the layer C may have a thickness of 0.02 to 0.03 inches, that is about 0.50 to 0.75 mm.

Figure 5:
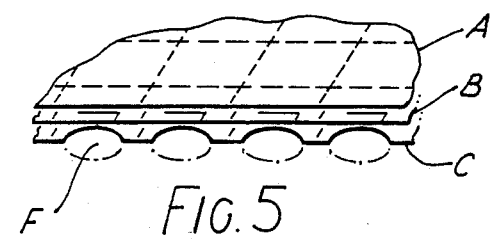

The operation of a non-return valve assembly according to the invention can be clearly seen from an inspection of FIGS. 4 and 5. As seen in FIG. 4 a flow of urine is permitted downwardly through the layer A, through an open flap D of each flap valve in the layer B, and through the hole F of the layer C. As seen in FIG. 5, flow in the reverse direction is inhibited or precluded because the respective flaps of the flap valve, when subjected to pressure from the underside, take an upward position in contact with the layer A and thus substantially close the flap valve holes in the layer B.

Figure 6:
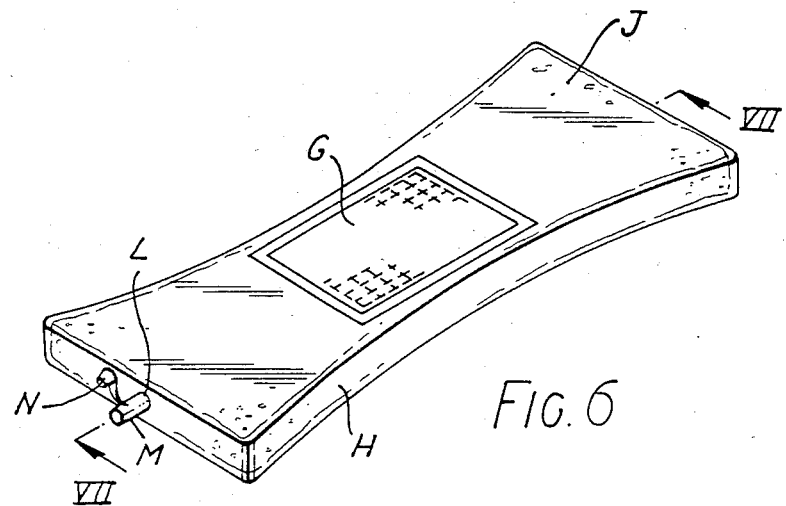
FIG. 6 is a diagrammatic perspective view showing one example of an incontinence pad assembly in accordance with the invention used in combination with a sponge within a waterproof cover.
Figure 7:
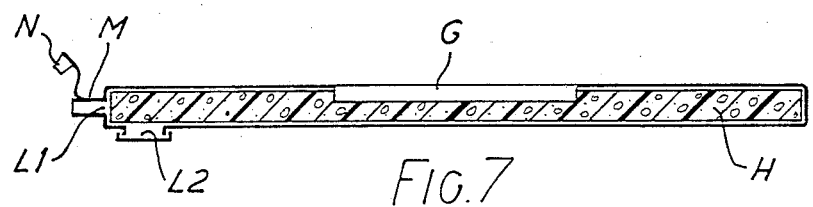
FIG. 7 is a cross-section in a central axial plane VII—VII in FIG. 6.

FIG. 6 is a perspective view showing a non-return valve assembly according to the invention placed on (and optionally secured to) one surface of a pad H of sponge material, the layer C of the assembly being juxtaposed in a face to face manner to the top face J of the sponge material H. The remainder of the sponge material H, that is to say the surfaces thereof except for that surface which is covered by the pad G, are encased in a waterproof outer cover or bag which may for example be a polythene or polyvinyl chloride film. An exit hole L, an exit tube M and a stopper N are provided. FIG. 7 shows two alternative possible positions L1 and L2 for the exit hole L.

In use, urine discharged by the wearer passes through the perforated layer A, through the flap valve layer B opening the flaps therein, through the holes F of the layer C, and into the sponge. By the use of a compressed sponge material as the pad H a considerable volume of urine may be accumulated. Thereafter, it may be emptied merely by squeezing, whereupon it is discharged through the outlet pipe M.

An important advantage of this invention is that the arrangement illustrated in FIGS. 6 and 7 could be worn by a patient, and would absorb a considerable quantity of urine. Moreover, as some available sponge materials have over 80% reabsorbtion, the device could be squeezed out and refitted, and the device would be to a large extent dry in wear as there is no possibility of any significant quantity of moisture being able to affect the skin of the wearer except over the limited surface area of the first layer A.

I claim:

1. A non-return valve assembly which includes at least three layers, the layers being secured together, the first layer being a sheet or film of perforated material, the second layer being a sheet or film of material having cuts therein defining an array of flap valves, and the third layer being a material having holes therein, each hole being in registry with an associated flap valve and being of a size of accommondate the flap of said valve, whereby said flap valves can open into said holes in said third layer.

2. An assembly according to claim 1 in which the flap valves are arranged in a regular rectangular array and each flap of a valve is defined by three cuts in the sheet material, the cuts constituting three sides of a rectangle so that the flap of the valve can pivot out of the plane of the sheet material generally about a rotational axis formed by the fourth side of the rectangle.

3. An assembly according to claim 1 in which the cuts are V-shaped.

4. An assembly according to claim 1 in which each cut is made up by a half or a major portion of the periphery of a circle or an ellipse.

5. An assembly according to claim 1 in which the first layer has a thickness substantially of 0.075 to 0.15 mm.

6. An assembly according to claim 1 in which the flap valves are arranged in linear rows.

7. An assembly according to claim 5 in which the second layer has a thickness substantially of 0.15 to 0.25 mm.

8. An assembly according to claim 7 in which the third layer has a thickness substantially of 0.50 to 0.75 mm.

9. An assembly according to claims 1 in which the first layer is polyethylene or an e.v.a. - polyethylene copolymer.

10. An assembly according to claim 9 in which the third layer is of soft ethylene vinyl acetate.

11. An assembly according to claim 1 in which the layers are integrated together by linear welds.

12. An assembly according to claim 11 in which the welds are made up by a series of spot or bar welds.

13. An assembly according to claim 1 in combination with a pad of sponge material located on the side of the third layer opposite to the second layer.

14. An assembly according to claim 13 in which the assembly is encased in a waterproof and liquid-proof covering except for an exposed portion of the first layer.

* * * * *